United States Patent [19]

Shibata et al.

[11] Patent Number: 4,714,555

[45] Date of Patent: Dec. 22, 1987

[54] AGENT FOR SEPARATION

[75] Inventors: Tohru Shibata; Ichiro Okamoto, both of Himeji, Japan

[73] Assignee: Daicel Chemical Industries, Ltd., Osaka, Japan

[21] Appl. No.: 24,877

[22] Filed: Mar. 11, 1987

Related U.S. Application Data

[63] Continuation of Ser. No. 696,137, Jan. 29, 1985, abandoned.

[30] Foreign Application Priority Data

Jan. 31, 1984 [JP] Japan .................................. 59-15760

[51] Int. Cl.$^4$ ............................................. B01D 15/08
[52] U.S. Cl. .................................... 210/635; 210/644; 210/656; 210/658; 210/198.2; 210/198.3; 210/500.29; 502/404
[58] Field of Search ............... 210/635, 636, 658, 644, 210/198.2, 198.3, 500.29; 502/404; 436/161, 162

[56] References Cited

U.S. PATENT DOCUMENTS

| | | | |
|---|---|---|---|
| 3,562,289 | 2/1971 | Battista | 210/656 |
| 3,597,350 | 8/1971 | Determann | 210/656 |
| 3,598,245 | 8/1971 | Determann | 210/656 |
| 3,657,118 | 4/1972 | Kraffczyk | 210/658 |
| 4,111,838 | 9/1978 | Schaeffer | 210/656 |
| 4,125,492 | 11/1978 | Cuatrecasas | 210/635 |
| 4,143,201 | 3/1979 | Miyashiro | 210/635 |
| 4,225,487 | 9/1980 | Cuatrecasas | 210/656 |
| 4,330,440 | 5/1982 | Ayers | 210/635 |
| 4,424,127 | 1/1984 | Roeraade | 210/198.2 |
| 4,448,691 | 5/1984 | Davis | 210/198.2 |
| 4,529,521 | 7/1985 | Cortes | 210/198.2 |

FOREIGN PATENT DOCUMENTS

| | | | |
|---|---|---|---|
| 2319495 | 1/1975 | Fed. Rep. of Germany | 210/656 |
| 7908056 | 6/1981 | Netherlands | 210/656 |

OTHER PUBLICATIONS

Segal, "Gel Permeation Chromatography and Cellulose, Effect of Degree of Nitration of Cellulose on Molecular Weight Distribution Data, Journal of Polymer Science, Part 1-A, vol. 8, 1970, pp. 23–35 (Microfilm).
Schneider, Aliphatic Alcohols Improve the Adsorptive Performance of Cellulose Nitrate Membranes–Application in Cheomatography and Enzyme Assays, Analytical Biochemistry, vol. 108, 1980, pp. 96–103, QP501A6.
Schneider, A., Micromethod for Estimation of Adenosine Deaminase and Adenosine Nucleosidase with Modified Cellulose Nitrate Membranes, Analytical Biochemistry, vol. 108, pp. 104–111, QPJ01A6.
Mike, Chromatographic and Allied Methods, Ellis Horwood Limited, Chichester, 1979, pp. 476–477.

*Primary Examiner*—Ernest G. Therkorn
*Attorney, Agent, or Firm*—Flynn, Thiel, Boutell & Tanis

[57] ABSTRACT

A nitrate or a nitrate group-containing derivative of polysaccharide is useful as a separating agent for a chemical substance, especially an optical isomer.

12 Claims, No Drawings

AGENT FOR SEPARATION

This application is a continuation of U.S. Ser. No. 696,137, filed Jan. 29, 1985, now abandoned.

The invention relates to a method for separating a chemical substance from a mixture containing the same, especially applied to resolution of optical isomers, and a separating agent therefor. The method is effected with use of a nitrate or a nitrate group-containing derivative of a polysaccharide. The substance to be resolved in the invention includes particularly optical isomers which could not be resolved directly in an easy manner in the prior art as well as common low-molecular weight compounds.

Generally, the physiological activity of a racemic compound often differs from that of a corresponding optically active compound. For example, in the fields of medicines, pesticides or the like, it is sometimes necessary to resolve optical isomers for the purposes of preventing adverse reactions and enhancing medicinal effects per unit dose. A mixture of optical isomers has been separated into its individual isomers by preferential crystallization or the diastereomer process. However, the varieties of the compounds which can be optically resolved by these processes are limited and most of these processes require a long time. Under these circumstances, development of a convenient chromatographic resolution process has eagerly been demanded.

It has been unknown in the prior art to use a polysaccharide nitrate as a resolving agent and, as a matter of course, this ester has not been used for the resolution of optical isomers.

The chromatographic resolution of optical isomers has been investigated for a long time from old times. For instance, cellulose and some of its derivatives have been used as column-chromatographic resolving agents in the optical resolution. These cellulose derivatives are those belonging to crystal system I, such as microcrystalline cellulose triacetate and carboxymethylcellulose.

However, such a cellulose or a derivative thereof could separate only a few substances. The separation power thereof was not sufficient.

The inventors have made intensive research and found that a polysaccharide nitrate effectively serves to separate various compounds, isomers and particularly optical isomers. The present invention has been completed on the basis of this finding.

Though the reason why the above-mentioned polysaccharide nitrates used in the present invention have an excellent effect of resolving optical isomers has not been elucidated yet, it may be possible that the inherent asymmetry of the polysaccharide, symmetry of the nitro group and the $\pi$-bonded system thereof will exert a great influence on the resolution of optical isomers.

In the invention, the polysaccharide may be natural or synthetic. Further a modified natural polysaccharide may be used. Preferable polysaccharides to be used in the invention include $\beta$-1,4-glucans such as cellulose, $\alpha$-1,4-glucans such as amylose and amylopectine, $\alpha$-1,6-glucans such as dextran, $\beta$-1,6-glucans such as pustulan, $\beta$-1,3-glucans such as curdlan and schizophyllan, $\alpha$-1,3-glucan, $\beta$-1,2-glucans such as Crown Gall polysaccharide, $\beta$-1,4-galactan, $\beta$-1,4-mannan, $\alpha$-1,6-mannan, $\beta$-1,2-fructans such as insulin, $\beta$-2,6- fructans such as levan, $\beta$-1,4-xylan, $\beta$-1,3-xylan, $\beta$-1,4-chitosan, $\beta$-1,4-N-acetylchitosans such as chitin, pullulan, agarose and alginic acid. Further cellulose, amylose, $\beta$-1,4-chitosan, chitin, $\beta$-mannan, $\beta$-1,4-xylan, inulin, curdlan and $\alpha$-1,3-glucan are more preferable since they are available with a high purity.

The number-average degree of polymerization of the polysaccharides is 3 to 5,000, preferably 10 to 1000 and particularly 10 to 500.

The nitrates or nitrate group-containing derivatives of polysaccharides used in the present invention can be prepared as follows.

As to cellulose nitrate, various processes for the preparation have been known as disclosed in detail in, e.g., "Dai-Yuki Kagaku", Vol. 19; Tennen Kobunshi Kagobutsu I, published by Asakura Book Store, p. 127 and Ott, Spurlin, "Cellulose" Part II, p. 715. In the most common process among them, a mixed acid comprising nitric acid or fuming nitric acid and conc. sulfuric acid is used. However, to obtain a substance having a particularly high degree of substitution and stability, a process wherein a mixture of phosphoric acid, fuming nitric acid and phosphorus pentoxide, i.e. so-called mixed phosphoric/nitric acid is used, is preferred as described in a thesis of Okawa et al. Further, new nitrating agents such as nitronium tetrafluoroborate ($NO_2^+BF_4^-$) which is a recently developed reagent for organic synthesis may be used for this purpose.

Amylose nitrate can be obtained in the same manner as in the preparation of cellulose nitrate ester (see "Dai-Yuki Kagaku", Vol. 20, Tennen Kobunshi Kagobutsu II published by Asakura Book Store, p. 164). Other polysaccharide nitrates may also be prepared in the same manner as above.

A mixed derivative of a polysaccharide may be obtained by esterifying a polysaccharide derivative having a substituent (other than the nitrate group) which is stable under the esterification conditions with nitric acid. In another process, a nitrate prepared by a conventional process is subjected to a further chemical treatment provided that the nitrate bonding is stable under reaction conditions for introducing a substituent other than the nitrate group. For example, cellulose nitrate acetate is obtained by this process wherein cellulose nitrate is treated with acetic anhydride in pyridine.

The non-nitrated hydroxyl groups in the polysaccharide nitrate of the present invention may be esterified, carbamoylated or etherified so far as its capacity of resolving isomers is not damaged.

In using the resolving agent of the present invention containing the polysaccharide nitrate as the principal component for the purpose of resolution, it is preferred to employ a chromatographic method. The preferred chromatographic methods include liquid and thin layer chromatographic methods. In using the resolving agent of the present invention in the liquid chromatography, there ma.y be employed a method wherein the polysaccharide nitrate of the present invention is fed into a column directly or in the form supported on a carrier, or a method wherein a capillary column is coated with said ester. Since the chromatographic resolving agent is preferably in the form of granules, the polysaccharide nitrate to be used as the resolving agent is preferably ground or shaped into beads. The particle size which varies depending on the size of a column or plate used is generally 1 $\mu$m to 10 mm, preferably 1 to 300 $\mu$m. The particles are preferably porous.

It is preferred to support the polysaccharide nitrate on a carrier so as to improve the resistance thereof to pressure, to prevent swelling or shrinkage thereof due to solvent exchange or to reduce the number of theoretical plates. The suitable size of the carrier which varies depending on the size of the column or plate used is generally 1 μm to 10 mm, preferably 1 to 300 μm. The carrier is preferably porous and has an average pore diameter of 10 Å to 100 μm, preferably 50 to 50,000 Å. The amount of the polysaccharide nitrate to be supported is 1 to 100 wt. %, preferably 5 to 50 wt. %, based on the carrier. A ratio of the pore size to the particle size in the carrier is preferred to be not more than 0.1.

The polysaccharide nitrate may be supported on the carrier by either chemical or physical means. The physical means include one wherein said ester is dissolved in a suitable solvent, the resulting solution is mixed with a carrier homogeneously and the solvent is distilled off by means of a gaseous stream under reduced pressure or heating and one wherein said ester is dissolved in a suitable solvent, the resulting solution is mixed homogeneously with a carrier and the mixture is dispersed in a liquid incompatible with said solvent by stirring to diffuse the solvent. The cellulose derivative thus supported on the carrier may be crystallized, if necessary, by heat treatment or the like. Further, the state of the supported polysaccharide nitrate and accordingly its resolving power can be modified by adding a small amount of a solvent thereto to temporarily swell or dissolve it and then distilling the solvent off.

Both porous organic and inorganic carriers may be used, though the latter is preferred. The suitable porous organic carriers are those comprising a high molecular substance such as polystyrene, polyacrylamide or polyacrylate. The suitable porous inorganic carriers are synthetic or natural products such as silica, alumina, magnesia, titanium oxide, glass, silicate or kaolin. They may be surface-treated so as to improve their affinity for said polysaccharide nitrate. The surface treatment may be effected with an organosilane compound or by plasma polymerization.

In using the polysaccharide nitrate of the present invention in the resolution of isomers, the resolving characteristics thereof may vary sometimes depending on physical properties thereof such as molecular weight, crystallinity, molecular orientation and polymorphism, even though they are chemically similar to one another. Therefore, natural polysaccharide which has been esterified under the heterogeneous reaction condition may be used without the dissolution method. A suitable solvent may be selected in a step of preparing a packing material or the polysaccharide nitrate may be subjected to a physical or chemical treatment such as heat treatment or etching in the course of or after imparting them with a shape suitable for the use.

As to the developers for the liquid chromatography, solvents in which the polysaccharide nitrate is soluble cannot be used. However, the developers are not particularly limited when the polysaccharide nitrate is chemically bound to the carrier or when it is cross-linked.

In the thin layer chromatogrpahy a layer having a thickness of 0.1 to 100 μm and comprising the resolving agent in the form of particles of about 0.1 μm to 0.1 mm and a small amount of a binder is formed on a supporting plate.

The polysaccharide nitrate may be spun into a hollow filament in which an eluent containing the compound to be resolved is allowed to flow so that the resolution is effected by virtue of the adsorption of the compound on the inner wall of the filament. In another embodiment, said ester is spun into an ordinary filament, which is then bundled in parallel and placed in a column so as to take advantage of the adsorption on the surface thereof. In the membrane resolution process, the resolving agent may be used in the form of a hollow filament or film.

The resolving agent of the present invention comprising the polysaccharide nitrate or its derivative of the present invention as a principal constituent is effective for the resolution of various compounds. Particularly, it is quite effective for the resolution of optical isomers which are quite difficult to resolve in the prior art. The optical isomers to be resolved are compounds having an asymmetric center or those having molecular asymmetry. Either one of the optical isomers to be resolved is selectively adsorbed on the aromatic ring-containing cellulose derivative.

The following examples will further illustrate the present invention, which by no means limit the invention. In the examples, the terms are defined as follows:

$$\text{volume ratio } (k') = \frac{[(\text{retention time of antipode}) - (\text{dead time})]}{(\text{dead time})}$$

$$\text{spearation factor } (\alpha) = \frac{\text{volume ratio of antipode adsorbed more strongly}}{\text{volume ratio of antipode Adsorbed less strongly}}$$

$$\text{rate of separation } (Rs) = \frac{2 \times (\text{distance between a peak of more strongly adsorbed antipode and that of less strongly adsorbed antipode})}{(\text{total band width of both peaks})}$$

EXAMPLE 1 (synthesis of cellulose trinitrate)

Cellulose nitrate (RS 1/16; a product of Daicel Ltd. having a degree of substitution of 2.2 and degree of polymerization of 40 to 50) was used as the starting material. An acid mixture comprising 98 ml of fuming nitric acid (specific gravity: 1.52), 103.5 g of orthophosphoric acid and 133 g of phosphorus pentoxide was prepared under cooling with ice and then stored at room temperature for 10 days. 3.6 g of cellulose nitrate was added to the mixture under cooling with ice. The mixture was left to stand for 30 min, immersed in a water bath at 16° to 17° C. for 60 min and then cooled with ice for 90 min. The product was added dropwise to 1.5 kg of crushed ice and the mixture was stirred well. After the ice had melted, cellulose trinitrate thus precipitated was collected with a glass filter and washed with water repeatedly. The product was stored in an aqueous sodium hydrogencarbonate solution. Each time of use, water was replaced with ethanol and then with methylene chloride and the liquid was evaporated under reduced pressure.

The resulting cellulose trinitrate exhibited a quite strong absorption in its I.R. spectrum at 1640 $cm^{-1}$ ($\nu_{N=O}$, as) 1270 $cm^{-1}$ ($\nu_{N=O}$, sym) and 830 $cm^{-1}$ $\nu_{N-O}$, sym) to suggest that it was a nitrate. Further, some strong absorptions were recognized in the range of 1000 to 1200 $cm^{-1}$ to suggest the presence of a cellulose skeleton. The absorption due to the hydroxyl group in the range of 3200 to 3700 $cm^{-1}$ was only slight to indicate that the nitration ratio was nearly 1.0.

EXAMPLE 2 (synthesis of cellulose trinitrate packing)

10 g of silica beads (Lichrospher SI 1000; a product of Merck & Co.) was placed in a 200 ml round-bottom flask with a side arm. After vacuum-drying in an oil bath at 120° C. for 3 h, $N_2$ was introduced therein. 100 ml of toluene which had been preliminarily distilled in the presence of CaH$_2$ was added to the silica beads. 3 ml of diphenyldimethoxysilane (KBM 202; a product of Shin'etsu Kagaku Co., Ltd.) was added to the mixture, stirred together and reacted with each other at 120° C. for 1 h. After distilling off 3 to 5 ml of toluene, the reaction was carried out at 120° C. for 2 h. The mixture was filtered through a glass filter, washed with 50 ml of toluene three times and then with 50 ml of methanol three times and dried in vacuum at 40° C. for 1 h.

About 10 g of the silica beads were placed in the 200 ml round-bottom flask with a side arm. After vacuum drying at 100° C. for 3 h, the pressure was returned to the atmospheric pressure and the mixture was cooled to room temperature. Then, N$_2$ was introduced therein and 100 ml of distilled toluene was added to the dried silica beads. 1 ml of N,O-bis(trimethylsilyl)acetamide (a trimethylsilylating agent) was added thereto and the mixture was stirred and reacted at 115° C. for 3 h.

The reaction mixture was filtered through a glass filter, washed with toluene and dried under vacuum for about 4 h.

1.20 g of cellulose trinitrate obtained in Example 1 was dissolved in 8.5 ml of 2-butanone, the silane-treated silica beads were impregnated with the resulting solution and the 2-butanone was reduced.

EXAMPLE 3

The silica beads supporting cellulose trinitrate obtained in Example 2 were packed in a stainless steel column having an inner diameter of 0.46 cm and a length of 25 cm by a slurry method. The high performance liquid chromatograph used was Trirotar-SR (a product of Nihon Bunko Kogyo Co., Ltd.) and the detector used was Uvidec-V. The flow rate was 0.5 ml/min and hexane-2/propanol mixture was used as the solvent. The results of the resolution of various racemic compounds are shown in Table 1.

TABLE 1

| Racemic compounds | Volume ratio ($k_1'$) | Resolution factor ($\alpha$) | Rate of separation (Rs) |
|---|---|---|---|
| 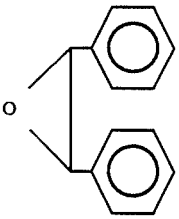 | 1.90 | 1.61 | 2.21 |
| 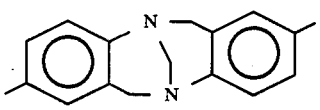 | 2.22 | 1.33 | 1.24 |
| 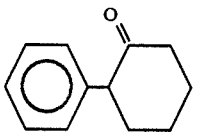 | 12.52 | 1.14 | 0.78 |
| 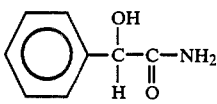 | 6.01 | 1.10 | 0.7 |

TABLE 1-continued

| Racemic compounds | Volume ratio ($k_1'$) | Resolution factor ($\alpha$) | Rate of separation (Rs) |
|---|---|---|---|
| 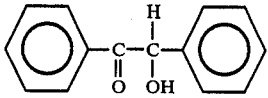 | 8.21 | 1 | — |
| 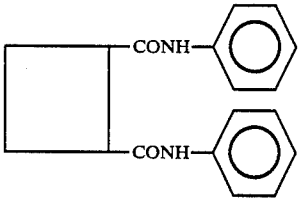 | 3.29 | 1.22 | 0.80 |
| 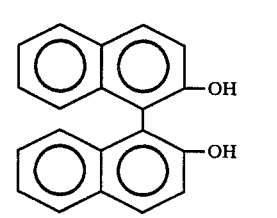 | 2.05 | 1 | — |

The embodiments of the invention in which an exclusive property or privilege is claimed are defined as follows:

1. A method of separating, by chromatography, an optical isomer from a racemic modification containing the same, which comprises the step of flowing a solution of said racemic modification in contact with cellulose trinitrate as a chromatographic resolving agent.

2. A method as claimed in claim 1, wherein said solution is flowed under liquid chromatographic conditions through a hollow filament of said cellulose trinitrate to effect separation.

3. A method as claimed in claim 1, wherein said solution is contacted under thin-layer chromatographic conditions with a plate coated with a layer comprising said cellulose trinitrate.

4. A method as claimed in claim 1, wherein said solution is flowed under liquid chromatographic conditions through a chromatographic column packed with spun filaments of said cellulose trinitrate, said filaments being bundled in parallel.

5. A method as claimed in claim 1 in which the cellulose trinitrate has a number-average polymerization degree of 3 to 5,000.

6. A method as claimed in claim 1, in which the method is conducted through a chromatographic column or layer comprising the cellulose trinitrate.

7. A method as claimed in claim 1 in which said solution is flowed, under liquid chromatography conditions, through a liquid chromatography column containing particles of said cellulose trinitrate having a particle size of from 1 micron to 10 millimeters whereby to separate said optical isomer.

8. A method as claimed in claim 7 in which said particles of cellulose trinitrate are deposited on a solid carrier in an amount of from 1 to 100 percent by weight, based on the weight of said carrier.

9. A method as claimed in claim 8, in which said carrier is porous, has a particle size of from 1 micron to 10 millimeters and has a pore size of from 10 Angstroms to 100 microns.

10. A method as claimed in claim 9 in which said carrier is silica beads.

11. A method as claimed in claim 7, wherein said column is packed with said cellulose trinitrate.

12. A method as claimed in claim 7, wherein said column is coated with said cellulose trinitrate.

* * * * *